(12) United States Patent  
Cadichon (10) Patent No.: US 7,553,289 B2
(45) Date of Patent: Jun. 30, 2009

(54) METHOD, APPARATUS, AND SYSTEM FOR BRACING A KNEE

(76) Inventor: Gregory Cadichon, 494 Thorndale Dr., Buffalo Grove, IL (US) 60089

( * ) Notice: Subject to any disclaimer, the term of this patent is extended or adjusted under 35 U.S.C. 154(b) by 54 days.

(21) Appl. No.: 11/708,289

(22) Filed: Feb. 20, 2007

(65) Prior Publication Data

US 2008/0200856 A1    Aug. 21, 2008

(51) Int. Cl.
  *A61F 5/00* (2006.01)
(52) U.S. Cl. .......................................... 602/23; 602/26
(58) Field of Classification Search ............... 602/5, 602/16, 20–23, 26–27; 128/882
  See application file for complete search history.

(56) References Cited

U.S. PATENT DOCUMENTS

| | | |
|---|---|---|
| 3,898,709 A | 8/1975 | Lewis et al. |
| 4,116,236 A | 9/1978 | Albert |
| 4,370,977 A | 2/1983 | Mauldin et al. |
| 4,372,298 A | 2/1983 | Lerman |
| 4,433,679 A | 2/1984 | Mauldin et al. |
| 4,624,246 A | 11/1986 | Ajemian |
| 4,665,905 A | 5/1987 | Brown |
| 4,817,588 A | 4/1989 | Bledsoe |
| 4,838,251 A | 6/1989 | Chignon et al. |
| 4,865,024 A | 9/1989 | Hensley et al. |
| 4,938,206 A | 7/1990 | Harris et al. |
| 4,961,416 A | 10/1990 | Moore et al. |
| 5,058,574 A | 10/1991 | Anderson et al. |
| 5,074,290 A | 12/1991 | Harris et al. |
| 5,352,190 A | 10/1994 | Fischer et al. |
| 5,458,565 A | 10/1995 | Tillinghast, III |
| 5,707,347 A | 1/1998 | Bixler |
| 6,074,355 A | 6/2000 | Bartlett |
| RE37,209 E | 6/2001 | Hensley et al. |
| 6,413,232 B1 | 7/2002 | Townsend et al. |
| 6,540,708 B1 | 4/2003 | Manspeizer |
| 2004/0006295 A1 | 1/2004 | Testa, Jr. et al. |
| 2004/0049291 A1* | 3/2004 | Deharde et al. ............... 623/46 |
| 2005/0070834 A1* | 3/2005 | Herr et al. ...................... 602/28 |
| 2005/0251079 A1* | 11/2005 | Carvey et al. .................. 602/26 |

* cited by examiner

*Primary Examiner*—Michael A. Brown
(74) *Attorney, Agent, or Firm*—Meroni & Meroni, P.C.; Charles F. Meroni, Jr.; Christopher J. Scott (57) ABSTRACT

A knee brace functions to extensionally center and thereby enhance patellar function. The brace comprises an upper bracket assembly, a lower bracket assembly, and certain torsional spring assemblies. The upper and lower bracket assemblies comprise leg-receiving bracket portions and certain axial support structure extending from the bracket portions to bracket junctions. Each spring assembly comprises a torsional spring element and an elastically compressible core element. The torsional spring elements compressibly receive the core elements. The torsional spring elements are actuable for imparting restorative resistance forces, and the core elements function to damp the restorative resistance forces. The damped restorative resistance forces function to safely enhance quadriceps muscle contraction during knee extension. The enhanced quadriceps muscle contraction functions to center the patella during knee extension, and thereby enhance patellar function. The brace may be attached to an anchored leg-covering garment for further restricting axial displacement relative to the leg.

23 Claims, 11 Drawing Sheets

METHOD, APPARATUS, AND SYSTEM FOR BRACING A KNEE

BACKGROUND OF THE INVENTION

1. Field of the Invention

The present invention generally relates to a knee brace. More particularly, the present invention relates to a knee brace for enhancing quadriceps muscle contraction during knee extension for centering the patella and thus enhancing patellar function.

2. Description of the Prior Art

As noted in U.S. Pat. No. 6,540,708 ('708 patent), the physiological motion of the human knee involves complex dynamic motion. Prior art knee bracing apparatuses and systems have attempted to control or otherwise manage the complex motions associated with knee extension, knee flexion, as well as polycentric motion more fully articulated in the '708 patent. Notably, the patella is typically stabilized by the insertion of the vastus medialis and the prominence of the anterior femoral condyles, which normally prevent lateral dislocation of the patella during flexion. Lateral dislocations do occur, however, given knee injury and other abnormal knee developments. Certain prior art patent discloses describing certain apparatuses and means for externally or superficially managing various forms of joint articulation, and particularly knee joint articulation, are briefly set forth hereinafter.

U.S. Pat. No. 4,370,977 ('977 patent), which issued to Mauldin et al., discloses a Knee and Elbow Brace. The '977 patent teaches an improved knee brace comprising thigh and calf cuffs and identical side members to simplify manufacture and permit use with a range of leg sizes. The hinge members on each of the side members permit the knee joint to be immobilized at a predetermined degree of flexion or movable within a predetermined arc of motion such as 0-degree to 30-degree flexion or 30-degree to 60-degree flexion. A tensioned cord is provided to urge the knee joint in a given direction. The spring force may be employed to inhibit the quadriceps muscles or permit progressive resistance exercises during rehabilitation. In a first modification, a torsion spring replaces the tension cord and forms the preferred embodiment. In a second modification, a torsion spring is also employed with a thumb screw which permits the knee joint to be immobilized at any desired degree of flexion. In a second embodiment, an elbow brace is provided for supporting and rehabilitation of the elbow joint and adjacent body portions in the arm. A hinge member permits pivotal motion of the elbow brace about an axis corresponding to the axis of the elbow joint. A spring provides a moment about the pivotal axis of the hinge member to inhibit the biceps muscle and provide a variable resistance to motion to rehabilitate the elbow joint and surrounding tissues.

Similarly, U.S. Pat. No. 4,433,679 ('679 patent), which issued to Mauldin et al., discloses a Knee and Elbow Brace. The '679 patent teaches a knee brace comprising a first hinge portion having a face comprising a plurality of circumferentially equally spaced teeth. An adjusting disc has a first circular face comprising teeth which mesh with the teeth of the first hinge portion to lock the component parts of the knee brace in any desired angular relationship. A second hinge portion has a face comprising a plurality of slots. The adjusting disc has a second circular face comprising a tooth which is selectively engageable with one of the slots of the second hinge portion to regulate angular movement between the component parts of the knee brace. A torsion spring has projections which are selectively positionable in apertures of the first and second hinge portions to apply a predetermined torque to the component parts of the knee brace.

U.S. Pat. No. 4,624,246 ('246 patent), which issued to Ajemian, discloses a Knee-Supporting Brace. The '246 patent teaches a knee-supporting brace comprising a pair of structures to be adapted to be fastened to a leg from both sides of the knee. Each structure includes two elongated solid members rotatably connected to each other which are adapted to be fastened respectively above and below the knee. Two springs connect these elongated members respectively between their upper ends and their lower ends so that the user must exert a force to stretch the springs but the compressed springs aid the user when the knee is straightened as the user stands up.

U.S. Pat. No. 4,665,905 ('905 patent) which issued to Brown, discloses a Dynamic Elbow and Knee Extension Brace. The '905 patent teaches a wire frame structure of two parallel aligned members formed into a compression spring centrally positioned to provide controlled force at each end. U-shaped yokes are adjustably affixed to the aligned members, one to each end. The yokes are hinged to cuffs suitable for attachment to human arm or leg members by self-fastening straps and adjacent the center springs, two additional securing straps are provided. In use, the brace assemblage provides a dynamic tension to apply a controlled force on an elbow or knee flexion contracture.

U.S. Pat. No. 4,817,588 ('588 patent), which issued to Bledsoe, discloses a Motion Restraining Knee Brace. The '588 patent teaches a motion restraining knee brace having a pair of articulated side portions each defined by elongated thigh and calf support members pivotally interconnected by an adjustable hinge mechanism. Each hinge mechanism has a single adjustment dial that cooperates with a pair of stop members to selectively limit the relative pivotal movement between the thigh and calf support members associated with the hinge. Outer ends of the thigh and calf support members are securable to the leg by connecting straps which encircle the leg and have independently adjustable anterior and posterior portions. Each of the thigh and calf support members is formed from two adjustably interlockable longitudinal sections releasably held together by a pivotable clip member to thereby provide for rapid support member length adjustment. To inhibit extension of the leg beyond the hinge established extension limit angle of the brace, a restraining strap member is looped through eyed connectors carried by each of the support members to form a generally hourglass-shaped strap network positioned behind the knee. As the leg is extended, the strap network is progressively tightened against it, with each portion of the network being held in essentially equal tension, to inhibit overextension of the leg.

U.S. Pat. No. 4,838,251 ('251 patent), which issued to Chignon et al., discloses a Dynamic Knee Brace. The '251 patent teaches a knee brace comprising a thigh-piece and a legging capable of pivoting between an extended position and a bent position, together with springs stretched over the sides of the brace between anchor elements fixed to the thigh-piece and the legging in order to urge the thigh-piece and the legging to pivot relative to each other towards at least one of said positions without impeding the movement thereof.

U.S. Pat. No. 4,865,024 ('024 patent), which issued to Hensley et al., discloses an Extension Deceleration Orthosis. The '024 patent teaches an extension deceleration orthotic fulcrum for knee and elbow braces, which simulates performance of the function of those ligaments that control joint motion and provide anteroposterior joint stability, comprising a lightweight, external spring assembly, upper and lower elongated arms, and centric or polycentric fulcrum, which is adjustable for its range of motion, adaptable for use on many different style orthoses, and whose strength can be varied to suit corrective, preventive, anthropomorphic, environmental, and usage requirements, including means both for mechanically dampening the limb's angular velocity on extension to prevent hyperextension and for accelerating the limb's angular velocity on flexion to enable quicker, smoother, less stressful motion. In one embodiment spring rods are assembled medially and laterally to conventional pairs of elongated orthotic brace arms to span the joint fulcrum point by serpentinely engaging novel roller posts, the assemblage thus serving to decelerate the limb during the last 15 to 20 degrees of extension, to help prevent the striking of a stop with its attendant risk of hyperextension, and thus serving to use the stored energy of the spring to facilitate flexion of the limb.

U.S. Pat. No. 4,938,206 ('206 patent), which issued to Harris et al., discloses a Floating Pivot Hinge and Knee Brace. The '206 patent teaches a knee brace comprising a thigh cuff having inner and outer spaced brace arms adapted to extend along the user's thigh toward the knee, a calf cuff including inner and outer spaced brace arms adapted to extend along the user's calf toward the knee, and floating pivot axis hinges rotatably connecting the inner and outer brace arms of each pair. The hinge is formed by a pair of juxtaposed hinge plates, each having a pivot face in opposition to a pivot face on the juxtaposed plate, with a concave groove in each of the face. A pivot bearing ball is confined between the opposed faces and retained in the concave grooves. A spring, bellville spring, or disk spring biases the hinge plates together when the pivot bearing ball is positioned in the opposed grooves between. The pivot bearing ball provides a floating pivot axis for hinge rotation of said hinge plates and thereby said braces relative to each other, the ball and concave grooves allowing the hinge plates simultaneously to slide and pivot relative to each other. The pivot axis floats between the hinge plates depending on the degree of pivoting and sliding movement in a wearer's knee joint as a result of flexion thereof.

U.S. Pat. No. 4,961,416 ('416 patent), which issued to Moore et al., discloses a Knee Brace. The '416 patent teaches a leg brace usable after knee ligament surgery utilizing first and second members which are held to the femoral and tibial portions of the leg. A hinge mechanism is also included in the brace for permitting pivotal rotation between the first and second members with the bending or flexion of the knee. A bar is extended across a selected portion of the leg. The bar is biased against the leg by a spring to prevent translation between the tibia and femoral for a particular angular range of extension of the knee portion of the leg.

U.S. Pat. No. 5,352,190 ('190 patent), which issued to Fischer et al., discloses a Knee Brace. The '190 Patent teaches an apparatus for use in bracing or exercising a knee joint in a manner that allows bending of the joint only along a predetermined path which approximates the natural bending of the joint. On one side of the joint are upper and lower struts that run along and are attached to the upper and lower leg and are attached to one another near the joint by a connecting mechanism which includes a set of linkage arms and telescoping elements that allow the struts to pivot relative to one another along the prescribed pivot line. On the other side of the joint are other upper and lower struts that run along and are attached to the upper and lower leg and are attached to one another near the joint by a ball and socket connector. The apparatus may be used as a brace or, alternatively, may be used with a cycling mechanism to cyclically flex and extend the joint or with a force-applying mechanism to apply a constant force urging the extension or flexing of the joint.

U.S. Pat. No. 6,074,355 ('355 patent), which issued to Bartlett, discloses a Knee Brace. The '355 patent teaches a testing device for determining the amount of tension in the quadriceps muscle for the anterior cruciate ligament to fail. There is also provided a knee brace having three point fixation and includes a pair of first arm members positioned on opposite sides of the knee joint. The lower leg brace member has a pair of second arm members oriented and positionable on opposite sides of the knee joint. The rigid thigh member and lower leg member are secured to the wearer's leg by means of a flexible strap extending around the back of the leg and adjustably attached thereto. The mating ends of the arms are connected by a pair of parallel spaced-apart face plates forming polycentric hinges which permit the mating ends of the arms to pivot about the connections. Various forms of extension cushions are provided to limit the proximity of the mating ends to one another to thereby limit the forward movement of the arms.

U.S. Pat. No. 6,413,232 ('232 patent), which issued to Townsend et al., discloses an Orthopedic Knee Brace having an Adjustable Knee Pad Support. The '232 patent teaches an orthopedic knee brace has a pair of femoral and tibial links, a hinge mechanism connecting the femoral and tibial links, a condylar knee pad support fixedly positioned on the lateral side of the brace and made adjustable by a spring-loaded ratchet mechanism featuring a series of interlocking teeth that allows for the axial displacement of the condylar pad to supply corrective force to the lateral knee joint and prevent of any unintended change in correction force. Moreover, in an effort to provide greater flexibility to the wearer in and enhance the stabilization of the design, the condylar pad is mounted for rotation about a point on the axis of the femoral condyle of the knee joint. The knee pad support may be adjusted by hand by rotating the ratchet mechanism to achieve the proper correction force or with an adjusting tool that engages a plurality of notches surrounding the periphery of the ratchet mechanism.

U.S. Pat. No. 6,540,708 ('708 patent), which issued to Manspeizer, discloses a Polycentric Joint for Internal and External Knee Brace. The '708 patent teaches an internal or external knee brace having a polycentric joint that enables control of a predetermined helicoidal motion and which permits compression and distraction of the knee joint. The knee brace includes a femoral component having a femoral joint member having at least one mating surface with a predetermined contour, and a stem projecting from the femoral joint member for attachment to the femur. The knee brace further includes a tibial component having a tibial joint member having at least one bearing surface for contact with the mating surface of the femoral component, and a stem projecting from the tibial joint member for attachment to the tibia. The joint members are arranged in a mounting member which has a spring or other resilient member located at one end which biases the tibial component toward the femoral component. The femoral component is fixed in the mounting member and the tibial component is rotatable relative to the fixed femoral component.

It will be seen from a further review of the above-referenced patents and other prior art generally known to exist relating to knee-bracing systems that the prior art perceives a need for a knee brace that functions to extensionally center and thereby enhance patellar function comprising an upper bracket assembly, a lower bracket assembly, and a pair of torsional spring assemblies, which torsional spring assemblies comprise elastically compressible core elements. By providing a torsional spring element with an elastically compressed core element, the actuation of a torsional spring element may be effectively damped for reducing stress on the treated joint.

SUMMARY OF THE INVENTION

Accordingly, it is an object of the present invention to provide a knee brace, as well as certain methodology and certain systemic considerations inherently taught by the knee brace. It is contemplated that the knee brace of the present invention may well function to extensionally center and thus enhance patellar function. The knee brace of the present invention preferably comprises an upper bracket assembly, a lower bracket assembly, and a pair of torsional spring assemblies. Systemically, the knee brace of the present invention may be attached both to a user's leg deep to the brace and a leg-covering garment superficial to both the user's leg and the knee brace. The leg-covering garment, as anchored to a user's waist, may further enhance the proper positioning of the brace so that proper patellar function may be maximized.

The upper bracket assembly comprises a U-shaped proximal-anterior-leg-receiving bracket portion, a proximal-medial support arm, and a proximal-lateral support arm. The lower bracket assembly comprises a U-shaped distal-posterior leg-receiving bracket portion, a distal medial support arm, and a distal-lateral support arm. The pair or first and second spring assemblies each comprise a torsional spring element, a core element, a core bracket, first and second proximal spring attachment posts, first and second distal spring attachment posts, certain post-fastening means, and certain assembly-fastening means.

The post-fastening means essentially function to fasten the spring attachment posts to the support arms of the upper and lower bracket assemblies. The core-fastening means function to fasten the spring core elements to the core brackets via the support arms of the upper and lower bracket assemblies. The torsional spring elements each comprise a proximal leg and a distal leg. The proximal leg is variably angled from the distal leg intermediate a relaxed spring angle (about 60 degrees) and a fully actuated spring angle (about 120 degrees). Certain preferred posts each comprise a longitudinal aperture or bore and a transverse aperture. Certain alternative posts are integrally formed with the support arms and comprise a longitudinal aperture or bore only. The proximal and distal legs are received in the posts.

The post-fastening means fasten the posts to the support arms of the upper and lower bracket assemblies such that the proximal support arms are variably angled relative to the distal support arms intermediate a relaxed arm angle (about 105 degrees) and a fully actuated arm angle (about 160 degrees). The torsional spring elements compressibly receive the core elements, and the proximal ends of the distal support arms and the distal ends of the proximal support arms are loosely sandwiched or received intermediate the spring core elements and the core brackets.

The proximal-anterior-leg-receiving portion may thus receive an upper leg, and the distal-posterior-leg-receiving portion may thus receive a lower leg. The torsional spring elements are actuable for imparting restorative resistance forces, which restorative resistance forces may well function to enhance quadriceps muscles contraction during knee extension, the enhanced quadriceps muscles contraction for centering the patella during knee extension. The knee brace of the present invention thus functions to extensionally center and enhance patellar function.

Certain methodology inherently taught by the present invention is thought to comprise certain steps for extensionally centering a patella and thereby enhancing patellar function, which steps comprise damping a torsional spring element assembly via an elastically compressed core element; bracing an upper and lower leg against proximal and distal ends of the torsional spring element assembly, as may be achieved by strapping the knee brace to a user's upper and lower leg with the torsional spring element assembly adjacent the knee joint; and actuating the damped torsional spring element assembly via knee extension. It is contemplated that the actuated and damped torsional spring element assembly thereby provides certain damped resistance for enhancing quadriceps muscle contraction and reducing patellar joint stress during knee extension.

Other objects of the present invention, as well as particular features, elements, and advantages thereof, will be elucidated or become apparent from, the following description and the accompanying drawing figures.

BRIEF DESCRIPTION OF THE DRAWINGS

Other features of my invention will become more evident from a consideration of the following brief descriptions of patent drawings.

DETAILED DESCRIPTION OF THE PREFERRED EMBODIMENT(S)

Referring now to the drawings, it is contemplated that the present invention inherently teaches a method, apparatus, and system for bracing a knee joint whereby the braced knee may be extended via enhanced contractual quadriceps action for extensionally centering and enhancing patellar function. It is noted that the patella 100 or kneecap is a thick, triangular bone which articulates with the femur and covers and protects the front of the knee joint as generally depicted and referenced in FIGS. 4-7. The patella 100 is attached to the tendon 101 of the quadriceps femoris muscle, which contracts to straighten or coaxially align the leg as further referenced in the noted figures.

The vastus intermedialis muscle is attached to the base of patella 100. The vastus lateralis and vastus medialis 102 are attached to lateral and medial borders of patella 100 respectively. It should be further noted that the patella 100 is stabilized by the insertion of vastus medialis 102 and the prominence of the anterior femoral condyles, which prevent lateral dislocation during flexion. The primary functional role of the patella 100 is knee extension. In this regard, the patella 100 increases the leverage that the tendon 101 can exert on the femur by increasing the angle at which it acts. Oftentimes, the patella 100 becomes laterally dislocated and the patellar joint must be rehabilitated to restore proper knee function. The method, apparatus, and system of the present invention are designed to restore proper patellar joint function for rehabilitating certain knee structure, particularly the vastus medialis 102 (as particularly depicted and referenced in FIGS. 4-7), to prevent lateral dislocation of the patella 100.

Central to the practice of the present invention is an improved knee brace 10 as generally illustrated and referenced in FIGS. 1-9. The knee brace 10 of the present invention preferably comprises an upper bracket assembly 11, a lower bracket assembly 12, and laterally-medially opposed torsional spring assemblies 13 all as further illustrated and referenced in FIGS. 1-3. The upper bracket assembly 11 preferably comprises a U-shaped, leg-receiving proximal bracket portion 14 or a proximal-anterior-leg-receiving bracket portion 14 (it being noted that the U-shaped proximal bracket portion functions to receive the anterior portion of the upper leg); and laterally-medially opposed proximal support arms 15 or a proximal-medial support arm 15 and a proximal lateral support arm 15 as generally illustrated and referenced in FIGS. 1-7. From an inspection of the noted figures, it may be seen that the proximal support arms 15 generally extend distally from the proximal bracket portion 14 and terminate at bracket junctions intermediate the upper and lower bracket assemblies 11 and 12.

The lower bracket assembly 12 preferably comprises U-shaped, leg-receiving distal bracket portion 16 or a distal-posterior leg-receiving bracket portion 16 (it being noted that the U-shaped distal bracket functions to receive the posterior portion of the lower leg); and laterally-medially opposed distal support arms 17 or a distal-medial support arm 17 and a distal-lateral support arm 17 as further illustrated and referenced in FIGS. 1-7. From an inspection of the noted figures, it may be readily seen that the distal support arms 17 generally extend proximally from the distal bracket portion 16 and terminate at bracket junctions intermediate the upper and lower bracket assemblies 11 and 12. The upper and lower bracket assemblies 11 and 12 may further preferably comprise certain pads 60 or padding as illustrated and referenced in FIG. 1 for reducing irritation that may otherwise occur due to interaction between bracket portions 14 and 16 with the underlying superficial derma (not specifically referenced).

Figure 1:
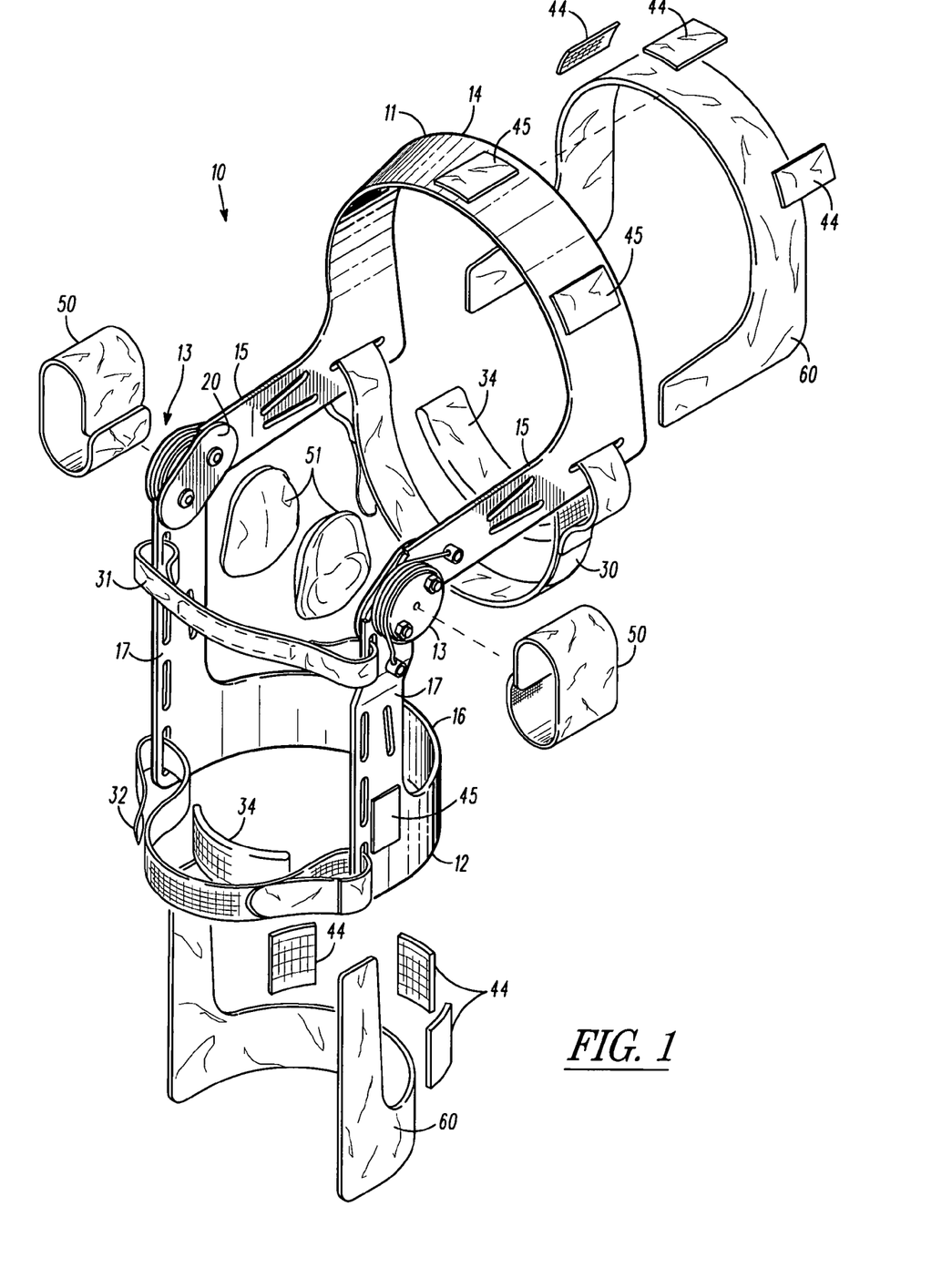
FIG. 1 is a top perspective view of the preferred brace assembly of the present invention with certain parts exploded therefrom for clarity.
Figure 2:
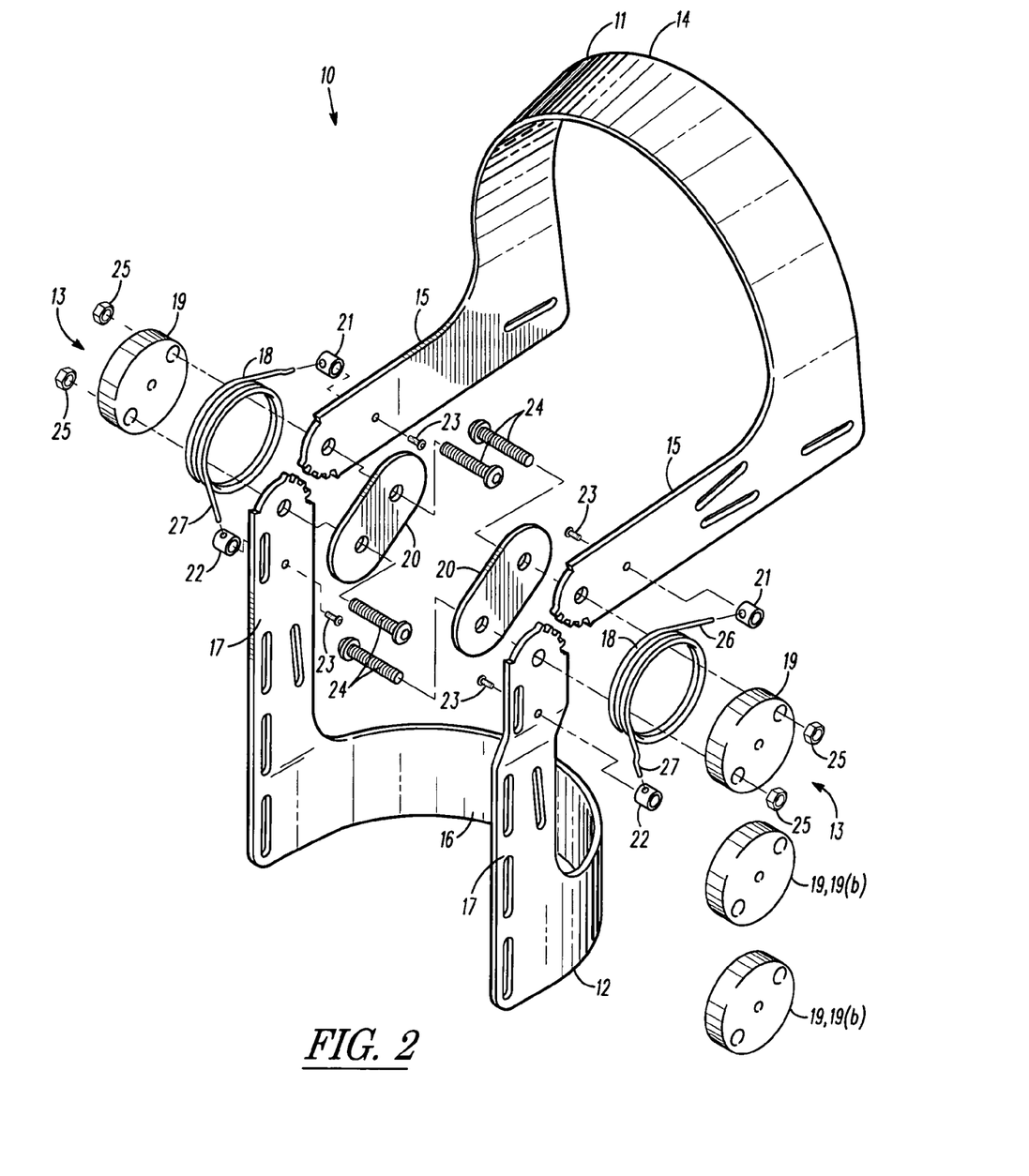
FIG. 2 is a top perspective exploded view of the preferred spring mounting system of the brace assembly of the present invention.
Figure 3:
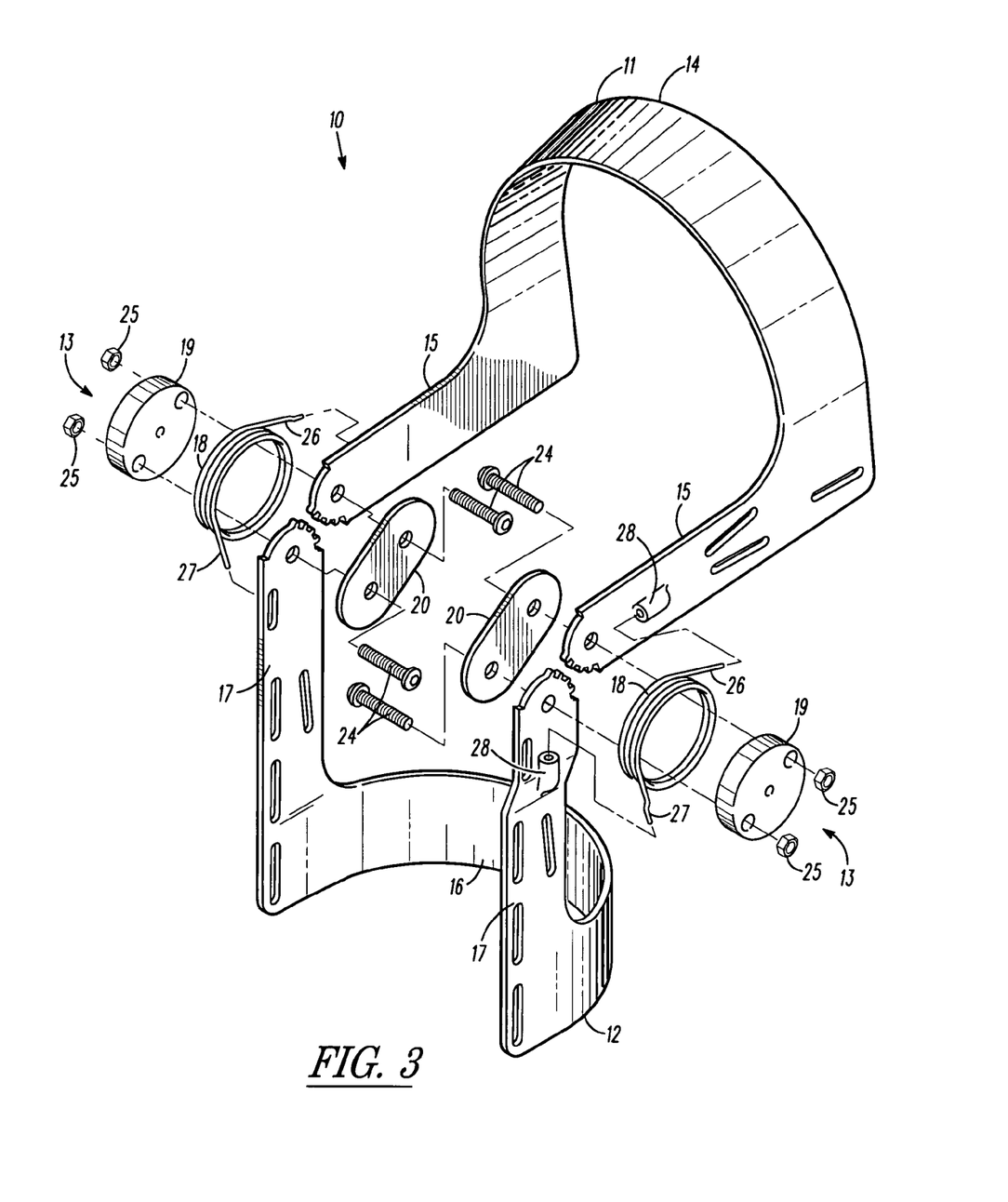
FIG. 3 is a top perspective exploded view of an alternative spring mounting system of the brace assembly of the present invention.

Each torsional spring assembly 13 preferably comprises a torsional spring element 18, an elastic core element 19, certain spring assembly-fastening means, and certain housing assemblies, as generally depicted and referenced in FIGS. 2 and 3. The torsional spring elements 18 are further depicted and referenced in FIGS. 5 and 7; and the core elements 19 are further depicted and referenced in FIGS. 6 and 8. From an inspection of FIG. 2, however, it will be seen that a plurality of core elements 19 are cooperable with each torsional spring element 18. In this regard, it should be noted that the core elements 19 as depicted in FIG. 2 are interchangeable and comprise or are constructed from varied materials. It is contemplated that each housing assembly may comprise an outer housing portion 50 and an inner housing portion 51 (as illustrated and referenced in FIG. 1, which portions 50 and 51 cooperate to enclose the spring torsional spring element(s) 18, the elastic core element(s) 19, and certain of the fastening means for maintaining the structural integrity of the spring assemblies 13 (as, for example, to prevent damage to the assemblies 13).

Figure 17:
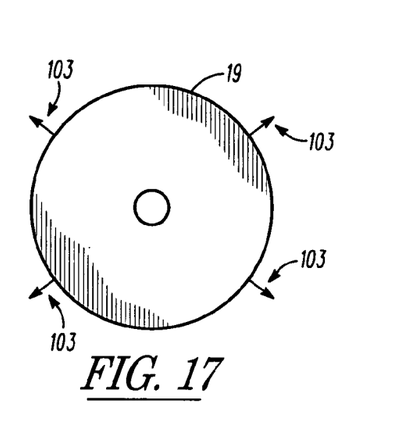
FIG. 17 is an axial view of the spring core element otherwise shown in FIG. 16 exploded therefrom to depict core element restoration forces.

In other words, the first or primary core element is interchangeable with secondary core elements 19(b), all of which comprise varied spring stiffness coefficients (they being preferably formed of an elastic material) for enabling the user or physical therapist to selectively modify or dampen the restorative resistance forces inherent in the torsional spring element 18. In other words, the core elements 19 each preferably comprise or are constructed from an elastic material, which elastic materials comprise select spring stiffness for variably restoring the core elements 19 to a relaxed core equilibrium state as generally depicted in the exploded views in FIGS. 2, 3, 12, and 15. When in an assembled state, the torsional spring elements 18 compressibly receive the core elements 19 thereby radially displacing the core elements 19 (inward) and imparting spring core restorative forces 103 (directed radially outward) as generally depicted in FIG. 17.

Figure 12:
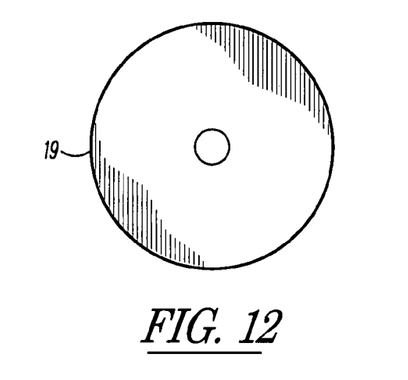
FIG. 12 is an axial view of a spring core element of the present invention in a relaxed state having a relaxed core diameter.
Figure 13:
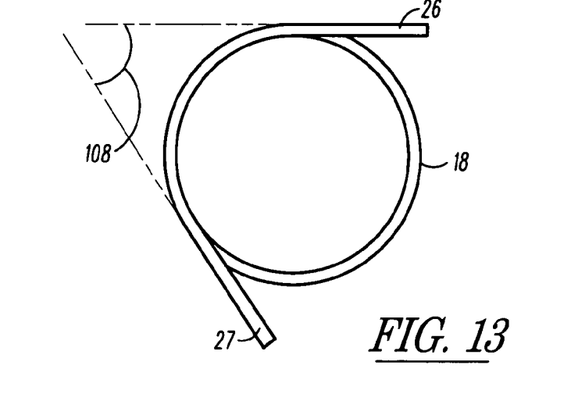
FIG. 13 is an axial view of a torsional spring element of the present invention in a relaxed state having a relaxed spring diameter smaller in magnitude than the relaxed core diameter.
Figure 14:
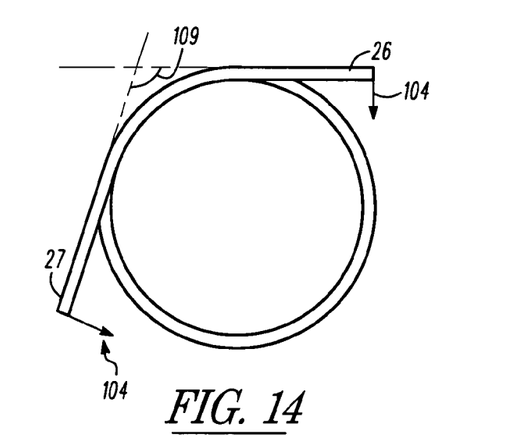
FIG. 14 is an axial view of the torsional spring element of the present invention in an actuated state having an actuated spring diameter greater in magnitude than the relaxed core diameter.

In this last regard, the reader is further directed to FIGS. 12-17, inclusive. FIG. 12 is an axial view of an elastic core element 19 in a relaxed equilibrium state. FIG. 13 is an axial view of a torsional spring element 18 in a relaxed equilibrium state. The diameter of the elastic core element 19 in a relaxed equilibrium state as depicted in FIG. 12 is (slightly) greater in magnitude than the diameter of the torsional spring element 18 in a relaxed state as generally depicted in FIG. 13. In order to properly receive elastic core element 19 for use in knee brace 10, the core element 19 must be radially inwardly compressed. It is contemplated that torsional spring element 18 may be actuated as generally depicted in FIG. 18, which is an axial view of the torsional spring element 18 in an actuated state.

Figure 15:
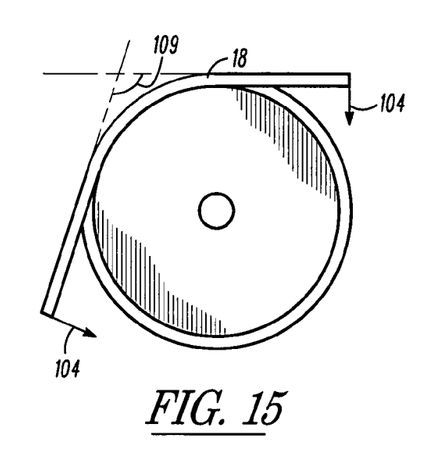
FIG. 15 is an axial view of the spring core element otherwise shown in FIG. 12 received in the torsional spring element otherwise shown in FIG. 14.
Figure 16:
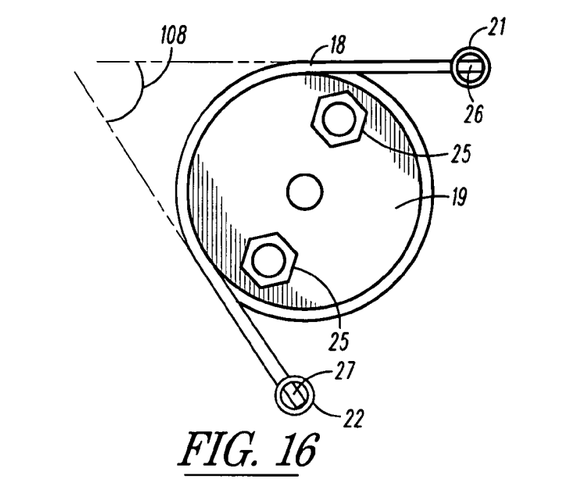
FIG. 16 is an axial view of the spring core element otherwise compressibly received in the torsional spring element, which torsional spring element is in a relatively relaxed state.

The torsional spring element 18, when in an actuated state may develop a larger diameter for receiving the relaxed state core element 19. Indeed, FIG. 15 is an axial view of the relaxed state core element 19 received in an actuated state torsional spring element 18. FIG. 16 is an axial view of a torsional spring assembly 13 depicting the torsional spring element 18 in a (relatively) relaxed equilibrium state and the core element in an actuated, radially inwardly compressed state. FIG. 17 is an axial view of the core element 19 otherwise depicted in FIG. 16 as exploded from FIG. 16 and showing the spring core restorative forces 103 radiating outwardly. It is contemplated that the spring core restorative forces 103 essentially function to modifying or dampen the restorative resistance forces 104 of the torsional spring element 18 when in an actuated state.

As alluded to above, certain spring assembly-fastening means are contemplated for fastening the spring assemblies 13 to the support arms 15 and 17 of the upper and lower bracket assemblies 11 and 12 at laterally-medially opposed bracket junctions. It is contemplated that the spring assembly-fastening means may be preferably defined in part or in whole by a core bracket 20 as illustrated and referenced in FIGS. 1-3; first and second proximal spring attachment posts 21 as illustrated and referenced in FIGS. 2, 4-8, 10, 11, and 16; first and second distal spring attachment posts 22 as illustrated and referenced in FIGS. 2, 4-8, 10, 11, and 16; certain post-fastening means such as screws or bolts 23 (as referenced in FIG. 2), and certain spring-fastening means such as screws or bolts 24 as referenced in FIGS. 2 and 3, which screws or bolts 24 are cooperatively associated with nuts 25 as referenced in FIGS. 2, 3, 5, 7, 10, 11, and 16.

The preferred posts 21 and 22 each comprises a longitudinal aperture or bore for receiving screws or bolts 23 and a transverse aperture for receiving the proximal end 26 or leg (posts 21) and distal end 27 or leg (posts 22) of torsional spring element 18 as generally depicted in FIGS. 1, 2, 4, 6, 8, and 16; and as specifically referenced in FIGS. 2 and 16. Alternative end-receiving posts 28 are illustrated and depicted in FIG. 3. It will be seen from an inspection of FIG. 3 that alternative posts 28 are contemplated and may be integrally formed with the support arms 15 such that the longitudinal axes of the posts 28 may effectively receive the proximal end 26 or leg and distal end 27 or leg of torsional spring element 18. The proximal end 26 or torsional spring element 18 is preferably variably angled from the distal end 27 of the torsional spring element 18 intermediate a relaxed spring angle 108 as generally depicted and referenced in FIGS. 4, 13, and 16; and a fully actuated spring angle 109 as generally depicted and referenced in FIGS. 6, 8, 14, and 15. It is contemplated that the preferred relaxed spring angle 108 may be defined by about a 60 degree angle and that the fully actuated spring angle may be defined by about a 120 degree angle.

Figure 4:
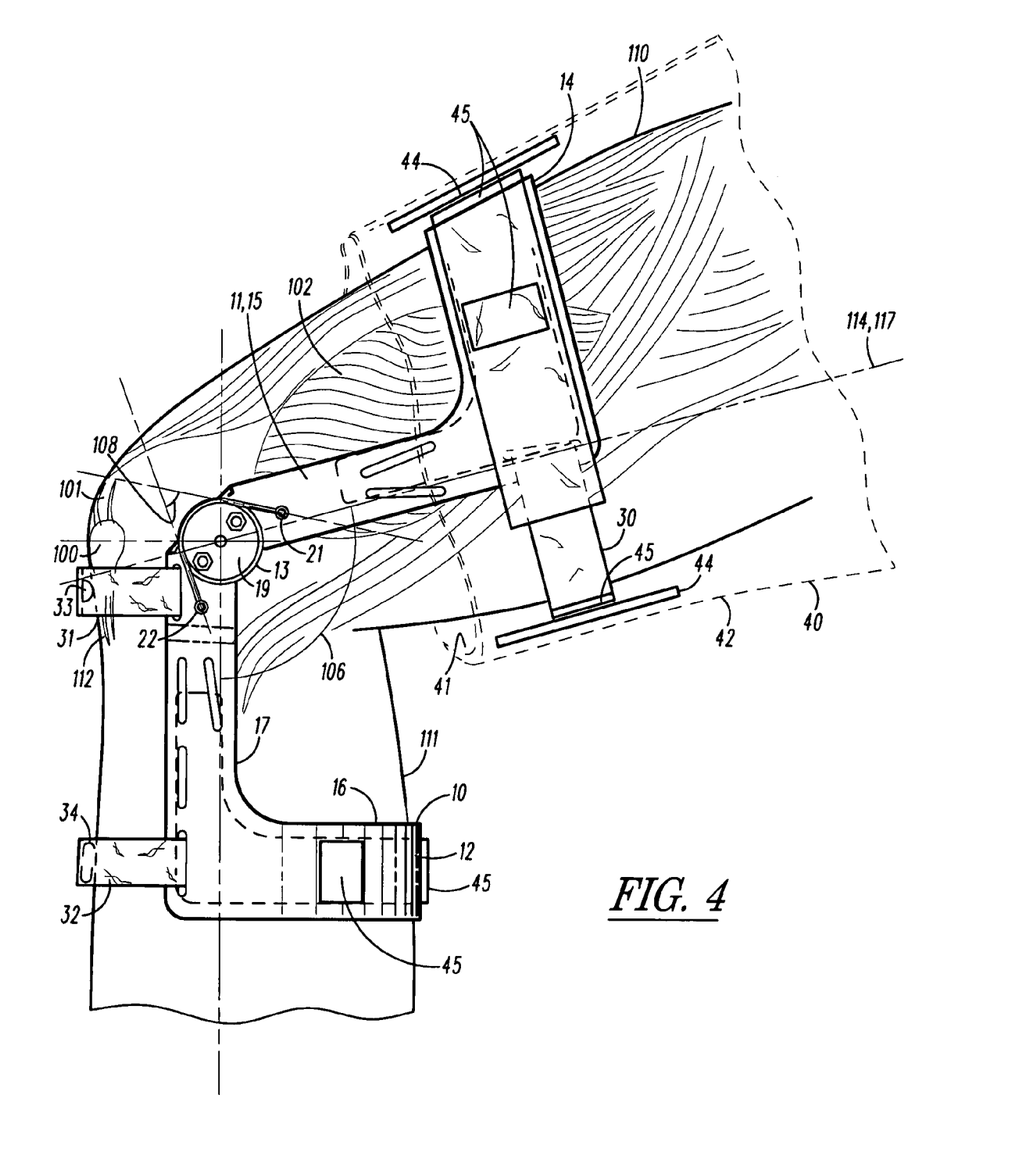
FIG. 4 a fragmentary medial side view depiction of the brace of the present invention attached to a right knee joint in a relaxed, knee-flexed position showing a shortened-length leg-covering garment and an enlarged sectional view of the junction intermediate the garment and brace.
Figure 6:
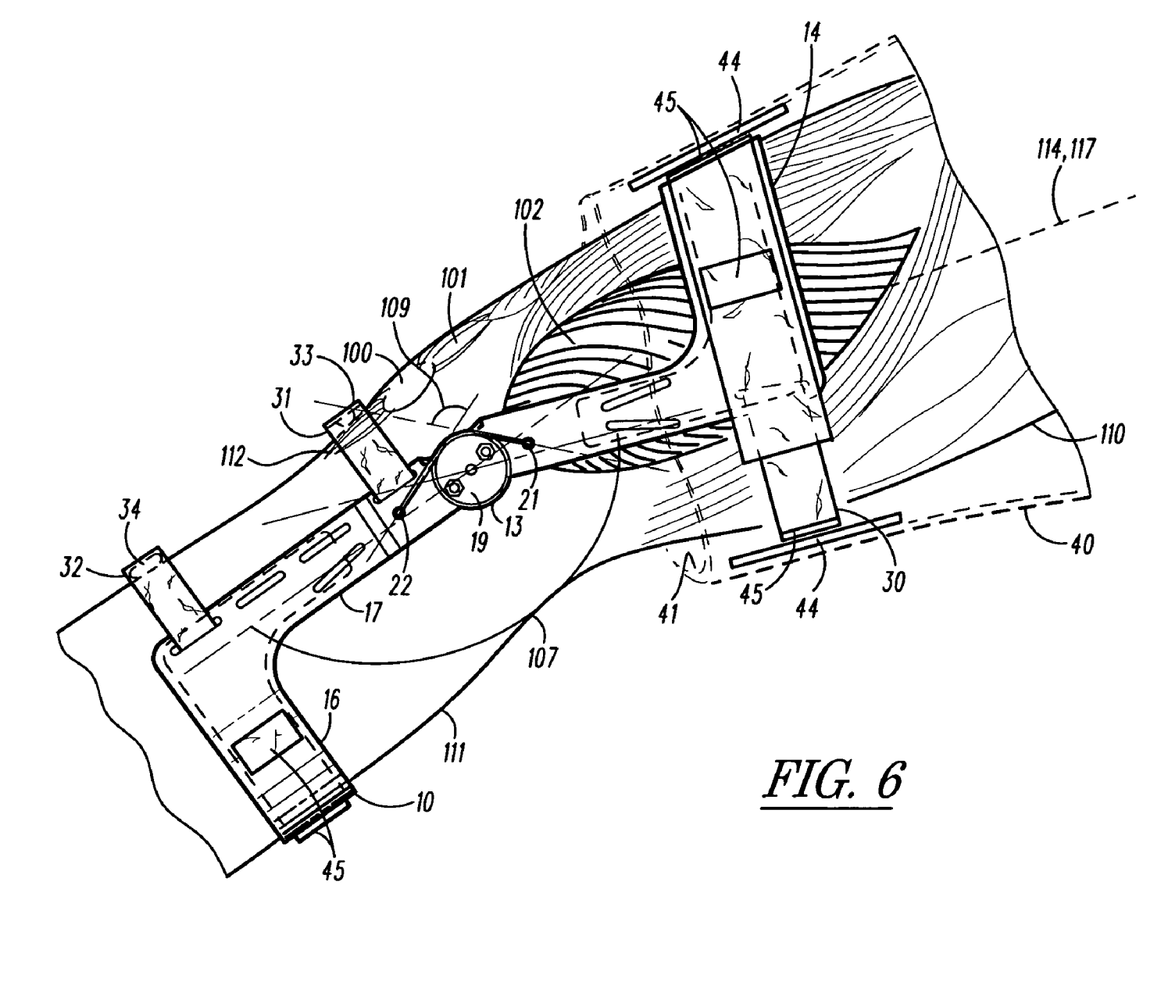
FIG. 6 is a fragmentary medial side view depiction of the brace of the present invention attached to a right knee joint in an actuated, knee-extended position and showing a shortened-length leg-covering garment.
Figure 7:
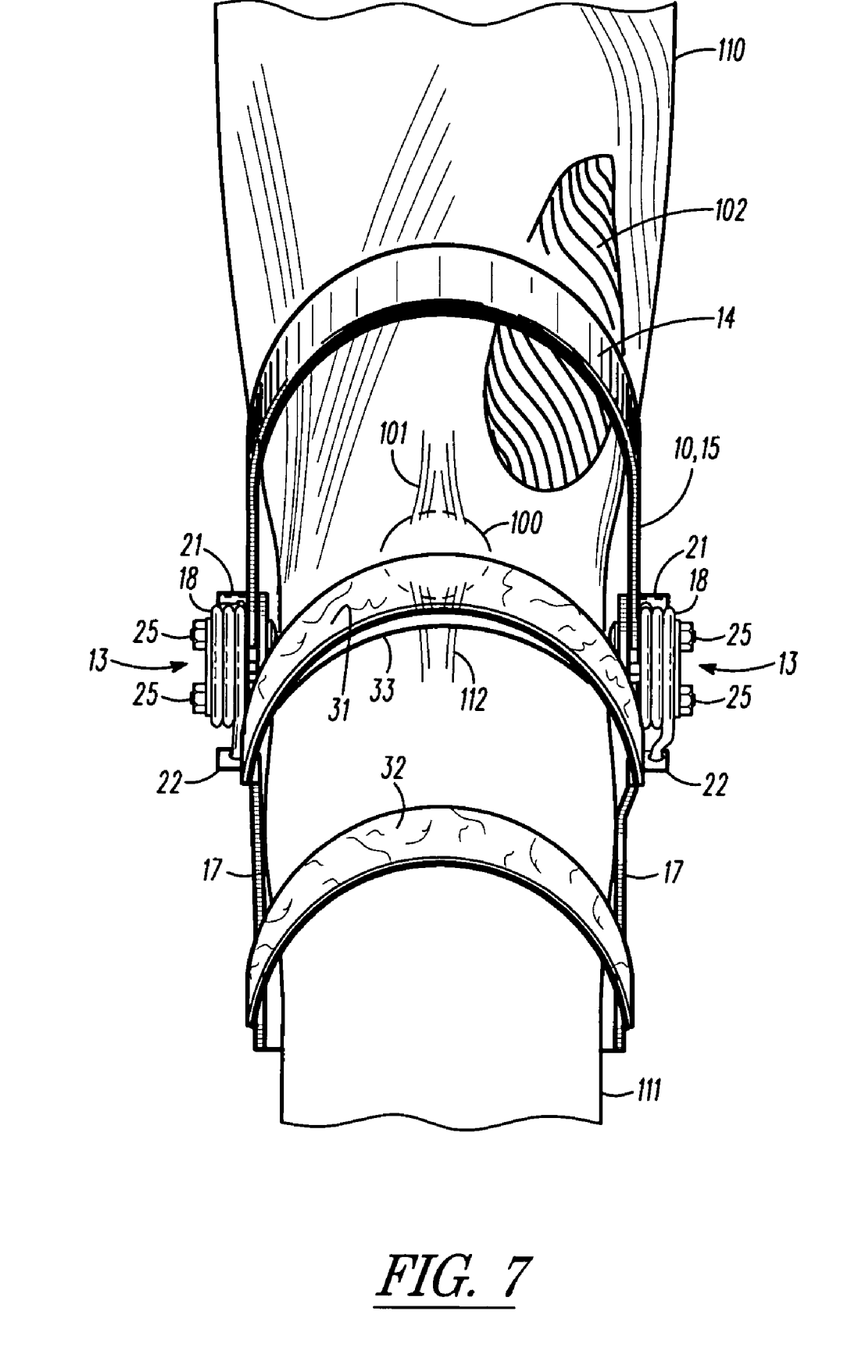
FIG. 7 is a fragmentary anterior view depiction of the brace otherwise shown in FIG. 6, showing the patella in a centered position and the vastus medialis quadriceps muscle in a contracted state.

The proximal and distal ends 26 and 27 legs are preferably received in the posts 21, 22, or 28 and the post-fastening means (whether screws or bolts 23 or whether integral formation) fasten the posts end-receiving posts to the support arms 15 and 17 of the upper and lower bracket assemblies 11 and 12 such that the proximal support arms 15 may be variably angled relative to the distal support arms 17 intermediate a relaxed arm angle 106 as generally referenced in FIG. 4 and a fully actuated arm angle 107 as generally referenced in FIG. 6. From an inspection of the noted figures, the reader will take note that the relaxed arm angle 106 is preferably on the order of about 105 degrees and the fully actuated arm angle is preferably on the order of about 160 degrees.

As earlier indicated, the core-fastening means such as screws or bolts 24 as referenced in FIGS. 2 and 3, which screws or bolts 24 are cooperatively associated with nuts 25 as referenced in FIGS. 2, 3, 5, 7, 10, 11, and 16. The core-fastening means function to fasten the spring core elements 19 to the core brackets 20 via the support arms 15 and 17 of the upper and lower bracket assemblies 11 and 12, and it should be recalled that the torsional spring elements 18 compressibly receive the core elements 19. The proximal ends of the distal support arms 17 and the distal ends of the proximal support arms 15 are preferably loosely sandwiched intermediate the respective spring core elements 19 and the core brackets 20 at the bracket junctions.

The proximal-anterior-leg-receiving bracket portion or proximal bracket portion 14 may thus receive an upper leg 110 and the distal-posterior-leg-receiving bracket portion or distal bracket portion 16 may thus receive a lower leg 111 as generally depicted and referenced in FIGS. 4-9. The upper and lower bracket assemblies 11 and 12 may preferably comprise certain strap means for retaining the upper and lower bracket assemblies 11 and 12 upon the upper and lower leg 110 and 111. It is contemplated that the strap means for retaining the upper and lower bracket assemblies 11 and 13 upon the upper and lower leg 110 and 111 may be preferably defined by adjustable retaining straps as generally depicted in FIGS. 1 and 4-11. The adjustable straps may be received through slots formed in the support arms 15 and 17 at varying locations along the length of the arms 15 and 17.

Notably, it is contemplated that the adjustable retaining straps of the present invention may preferably comprise a proximal-leg-retaining strap 30 or a proximal-posterior-leg-retaining strap as illustrated and referenced in FIGS. 1, 4, 6, and 8; and two distal-leg-retaining straps, including a proximal-anterior retaining strap 31 cooperable with the proximal end of the lower bracket assembly 12 as illustrated and referenced in FIGS. 1, 4-8, 10, and 11; and a distal-anterior retaining strap 32 cooperable with the distal end of the lower bracket assembly 12 as illustrated and referenced in FIGS. 1 and 4-8. It is contemplated that the lower bracket assembly 12 may benefit from axially spaced retention straps given that the primary functional role of the patella 100 is knee extension (i.e. coaxial alignment of the lower leg 111 with the upper leg 110) or primary movement of the lower leg 111 relative to the upper leg 110 about the knee joint. Straps 30 and 32 may further comprise certain padding as at 34 (in FIG. 1) for reducing irritation that may otherwise occur due to interaction between straps 30 and 32 with the superficial derma (not specifically referenced).

It is further contemplated that the first distal-leg-retaining strap or the proximal-anterior retaining strap 31 may preferably comprise certain tendon-retaining means for limiting movement of the patellar ligament 112 as generally depicted and referenced in FIGS. 4-8, 10, and 11. In this regard, it is contemplated that strap 31 may preferably comprise a bulk element 33 for pressing into the patellar ligament 112 in superior adjacency to the tibial tuberosity as further illustrated and referenced in FIGS. 4-8, 10, and 11. It is contemplated that the tendon-retaining means may well function to restrict movement of a patellar ligament or tendon 112 of the lower leg 111 and thus function to further enhance patellar function.

Properly positioning a knee brace adjacent a knee joint is central to practice of any knee brace art. As a means to enhance the effectiveness of the knee brace 10 of the present invention it is contemplated that the knee brace 10 of the present invention may be attached (via certain garment-attachment means) to a leg-covering garment 40 as generally illustrated and referenced in FIGS. 4, 6, 8, and 9. It is contemplated that the leg-covering garment 40 may be thought to preferably comprise a brace-attaching inner garment surface 41, a brace-concealing outer garment surface 42, a garment axis 117 (all as further depicted and referenced in FIGS. 4, 6, 8, and 9), and certain means for preventing axial garment displacement. It is contemplated that the means for preventing axial garment displacement may be preferably defined by a belt 43 as illustrated and referenced in FIG. 9, an elastic band, a tie cord, a tie strap, or similar other article for anchoring a leg-covering garment (such as trousers or shorts) about the user's waist.

Figure 8:
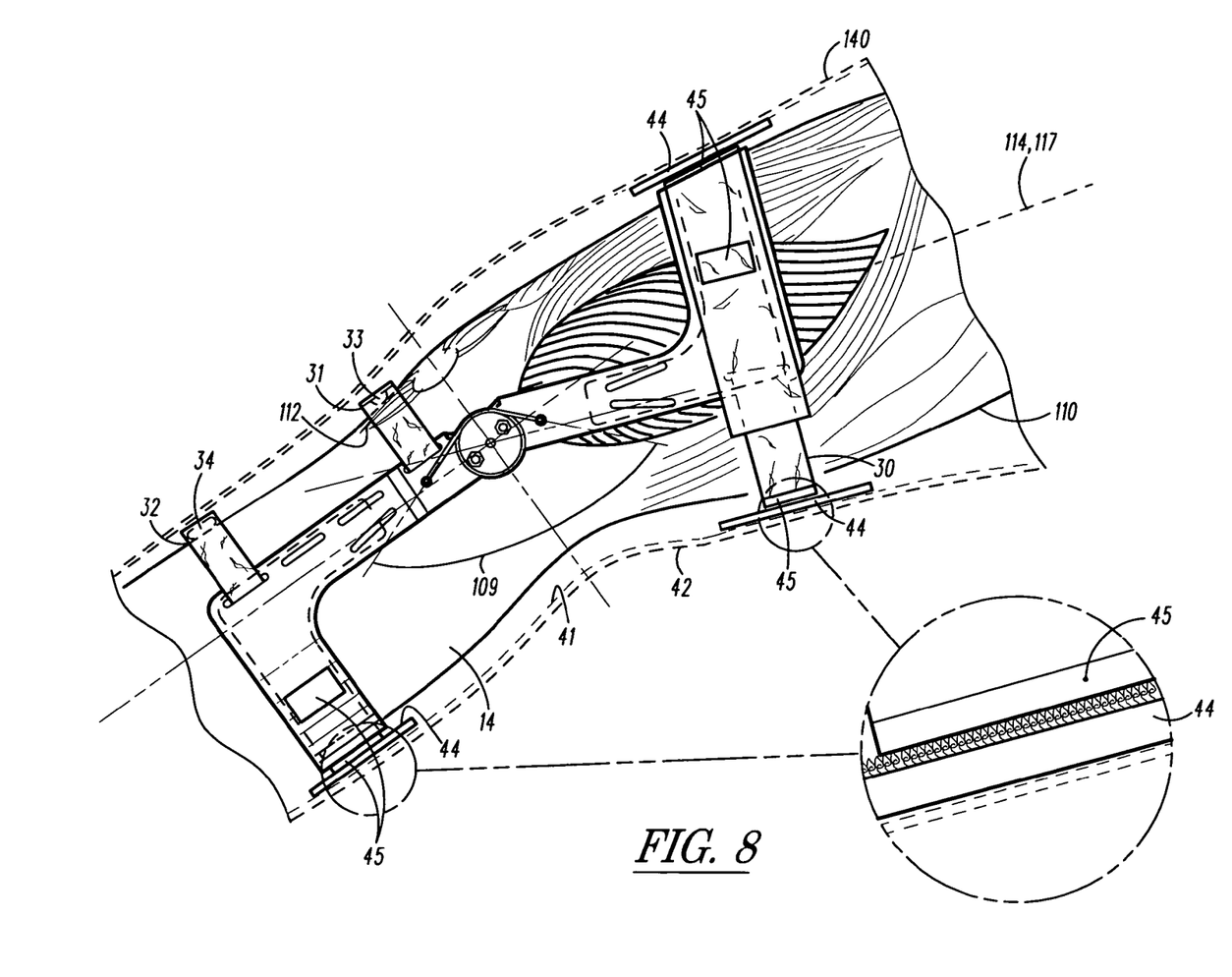
FIG. 8 is a fragmentary medial side view depiction of the brace of the present invention attached to a right knee joint in an actuated, knee-extended position and showing a full-length leg-covering garment and an enlarged sectional view of the junction intermediate the garment and brace.
Figure 9:
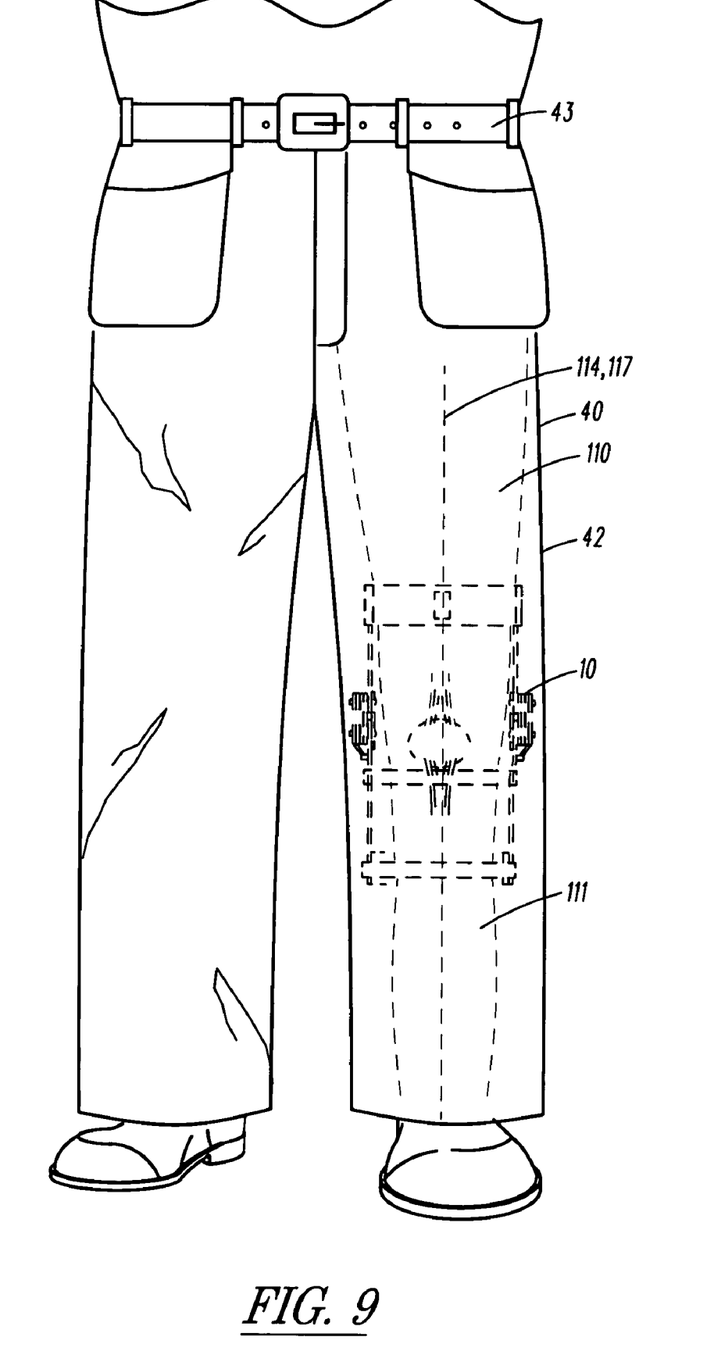
FIG. 9 is a fragmentary anterior view of a user donning the knee brace of the present invention in which the knee brace is shown in broken lines attached to leg also shown in broken lines to depict otherwise hidden structure.

It is contemplated that the inner garment surface is juxtaposable in superficial adjacency to a user's leg as donned with the knee brace 10, and that the garment axis 117 being coaxially alignable with (or parallel to) the leg axis 114 as generally depicted in FIGS. 8 and 9. It is further contemplated that the garment-attachment means maybe preferably defined by VELCRO brand hook and loop fastening material or similar other type hook and loop fasteners, although snaps, buttons, and similar other means of garment-attachment could conceivably perform the function. In this regard, the reader is directed to FIG. 1, which figure depicts certain hooked material as at 44 and certain looped material as at 45. It is contemplated that the looped material 45 may be adhesively attached to the outer surface of the leg-receiving bracket portions 14 and 16 and that the hooked material 44 may be stitched or otherwise attached to the inner garment surface 41. It is thus contemplated that the garment attachment means may effectively function to removably attach the knee brace 10 to the inner garment surface 41 for restricting axial brace displacement relative to the garment axis 117. Together, the means for preventing axial garment displacement (such as a belt 43) and the garment attachment means (such as hook and loop fastening means) may well function to retain the knee brace 10 upon the upper and lower leg at the prescribed position.

Figure 5:
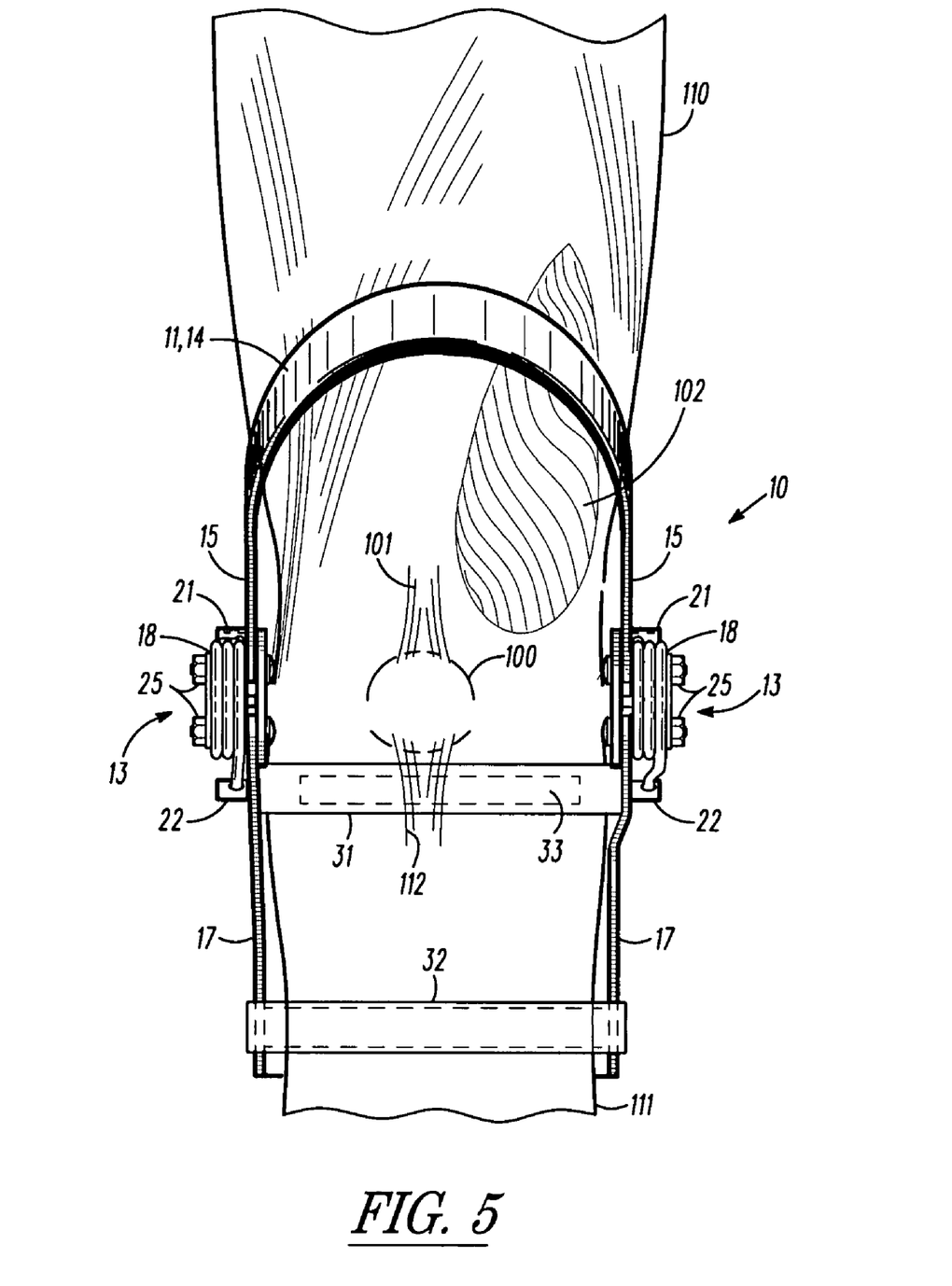
FIG. 5 is a fragmentary anterior view depiction of the brace otherwise shown in FIG. 4, showing the patella in a slightly offset, non-centered position and the vastus medialis quadriceps muscle in a relaxed state.
Figure 10:
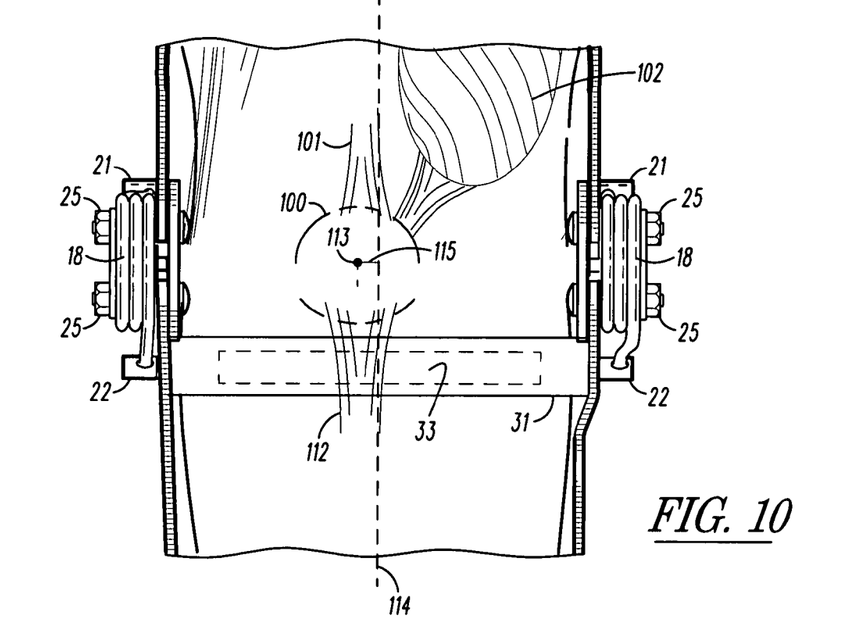
FIG. 10 is a fragmentary enlarged anterior view depiction of the knee joint otherwise shown in FIG. 5, showing the patella in a slightly offset, non-centered position and the vastus medialis quadriceps muscle in a relaxed state.
Figure 11:
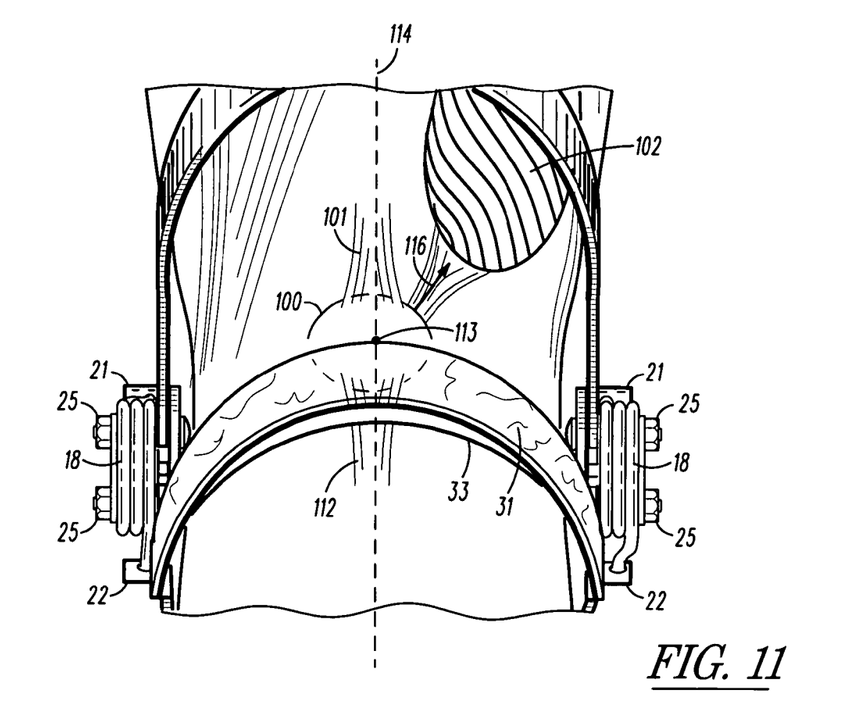
FIG. 11 is a fragmentary enlarged anterior view depiction of the knee joint otherwise shown in FIG. 7, showing the patella in a centered position and the vastus medialis quadriceps muscle in a contracted state.

The torsional spring elements 18 are thus actuable intermediate a relaxed state and a fully actuated state for imparting restorative resistance forces (such as forces 104), which forces may well enhance quadriceps muscle contraction (particularly the vastus medialis) during knee extension as comparatively depicted in FIGS. 4 and 5 (depicting the vastus medialis in a relaxed state) versus 6-8 (depicting the vastus medialis in a contracted state); and FIG. 9 (depicting the vastus medialis in a relaxed state) versus FIG. 10 (depicting the vastus medialis in a contracted state). From an inspection of FIGS. 9 and 10, it will be seen that when the vastus medialis is in a relaxed (knee flexed) state, the patella may become slightly off-centered or laterally disclosed as generally depicted at 115.

In other words the center 113 of patella 100 may become laterally displaced relative to a leg axis as depicted and referenced at 114. When the vastus medialis is contracted as depicted in FIG. 10, it operates to force (as at vector 116) the patella back to center having proximal (+y-axis) and medial (+x-axis) components. Notably, the vastus medialis is the muscle that extends the leg the last ten percent and thus it is key to proper patellar functioning. The knee brace 10 of the present invention may thus function to center the patella 100 during knee extension and may thus be said to operate extensionally centering and enhancing patellar function.

While the foregoing specifications contain much specificity, this specificity should not be construed as limitations on the scope of the invention, but rather as an exemplification of the invention. For example, as is implicit in the foregoing descriptions the present disclosure may further be said to disclose a knee brace for extensionally centering and enhancing patellar function, the knee brace comprising an upper bracket assembly, a lower bracket assembly, and at least one spring assembly. The upper bracket assembly may be said to essentially comprise a leg-receiving proximal bracket portion (such as bracket portion 14) and certain proximal axial support structure (such as support arms 15). The proximal axial support structure extends distally from the proximal bracket portion. Similarly, the lower bracket assembly may be said to essentially comprise a leg-receiving distal bracket portion (such as distal bracket portion 16) and certain distal axial support structure (such as support arms 17), which distal axial support structure extends proximally from the distal bracket portion.

Each spring assembly comprises a torsional spring element and an elastically compressible core element. Each torsional spring element compressibly receives the core element and comprises proximal and distal ends. Each proximal end is preferably attached to the proximal axial support structure, and each distal end is preferably attached to the distal axial support structure. The proximal bracket portion is sized and shaped to receive an upper leg, and the distal bracket portion is sized and shaped to receive a lower leg. Each torsional spring element is actuable for imparting restorative resistance forces, and each core element functions to damp said restorative resistance forces. It is contemplated that the damped restorative resistance forces may well function to enhance quadriceps muscle contraction during knee extension, which enhanced quadriceps muscle contraction functions to center the patella during knee extension.

The core element(s) may be interchangeable with at least one or more secondary core element(s), all of which may comprise varied varied spring stiffness coefficients. The variable spring stiffness coefficients and varied materials comprising the core elements may well enable the user to selectively modify or damp the restorative resistance forces. Further, certain garment attachment means of the present invention may well function to removably attach the knee brace to a separately anchored (e.g. via a belt-anchored scenario) leg-covering garment such as trousers or shorts. The knee brace, being removably attachable to the leg-covering garment, is thereby restricted from axial displacement relative to the upper and lower leg, and the garment attachment means may thus function to further retain the upper and lower bracket assemblies upon the upper and lower leg.

Certain methodology inherently taught by the knee brace of the present invention is further contemplated to comprise certain steps for extensionally centering a patella and thereby enhancing patellar function, which steps comprise damping a torsional spring element assembly via an elastically compressed core element compressibly received in or by the torsional spring element. The elastically compressed core element functions to modify or dampen the resistance forces otherwise experienced via the actuated torsional spring member(s). The upper and lower leg may then be braced against the proximal and distal ends of the torsional spring element assembly, as may be achieved by strapping the knee brace to a user's upper and lower leg with the torsional spring element assembly adjacent the knee joint. By way of actuating the damped torsional spring element assembly via knee extension, it is contemplated that the actuated and damped torsional spring element assembly may provide certain damped resistance for enhancing quadriceps muscle contraction and reducing patellar joint stress during knee extension.

The step of damping the torsional spring element may be further defined by selectively choosing a damping element (such as core element 19 or 19(*b*)), the damping element being selectively chosen from a damping element group, the damping element group comprising damping elements, the damping elements being formed from various elastic materials having varied stiffness coefficients. The selected damping element may then be cooperably associated with the torsional spring element for damping said torsional spring element.

The damping elements or core elements may be compressibly and interchangeably receivable by the torsional spring element for damping the torsional spring element. Further, the step of bracing the upper and lower leg against the proximal and distal ends of the torsional spring element assembly may comprise or involve the steps of anchoring a leg-covering garment in superficial adjacency to the torsional spring element assembly and anchoring the torsional spring element assembly to the leg-covering garment so as to prevent axial displacement of the torsional spring element assembly or knee brace.

Thus, although the invention has been described by reference to a preferred embodiment, certain systemic considerations, and certain methodology, it is not intended that the novel teachings set forth in the foregoing disclosure be limited thereby, but that modifications thereof are intended to be included as falling within the broad scope and spirit of the foregoing disclosure, the following claims and the appended drawings.

I claim:

1. A knee bracing system, the knee bracing system for extensionally centering and enhancing patellar function, the knee bracing system comprising, in combination:

a knee brace, the knee brace comprising an upper bracket assembly, a lower bracket assembly, and laterally-medially opposed spring assemblies, the upper bracket assembly comprising a leg-receiving proximal bracket portion and laterally-medially opposed proximal support arms, the proximal support arms extending distally from the proximal bracket portion, the lower bracket assembly comprising a leg-receiving distal bracket portion and laterally-medially opposed distal support arms, the distal support arms extending proximally from the distal bracket portion, each spring assembly comprising a torsional spring element, a core element, and spring assembly-fastening means, the torsional spring elements receiving the core elements, the spring assembly-fastening means fastening the spring assemblies to the support arms of the upper and lower bracket assemblies at laterally-medially opposed bracket junctions, the proximal bracket portion for receiving an upper leg, the distal bracket portion for receiving a lower leg, the upper and lower leg being coaxially alignable to define a leg axis;

a leg-covering garment, the leg-covering garment comprising an inner garment surface, a garment axis, and means for preventing axial garment displacement, the inner garment surface being juxtaposable in superficial adjacency to the knee brace, the garment axis being coaxially alignable with the leg axis; and garment-attachment means, the garment attachment means for removably attaching the knee brace to the inner garment surface and for restricting axial brace displacement relative to the garment axis, the means for preventing axial garment displacement and the garment attachment means for axially positioning the knee brace upon the upper and lower leg, the torsional spring elements being actuable for imparting restorative resistance forces, the restorative resistance forces for enhancing quadriceps muscle contraction during knee extension, the enhanced quadriceps muscle contraction for centering the patella during knee extension and for coaxially aligning the upper and lower leg, the knee bracing system thus for extensionally centering and enhancing patellar function.

2. The knee bracing system of claim 1 comprising strap means for retaining the upper and lower legs in the proximal and distal bracket portions.

3. The knee bracing system of claim 2 wherein the strap means for retaining the upper and lower legs in the proximal and distal bracket portions are defined by adjustable retaining straps, the adjustable retaining straps comprising a proximal-leg-retaining strap and first and second distal-leg-retaining straps, the lower bracket assembly comprising a distal end and a proximal end, the first distal-leg-retaining strap being cooperable with the proximal end and the second distal-leg-retaining strap being cooperable with the distal end, the adjustable retaining straps for enhancing retention of the upper and lower legs in the proximal and distal bracket portions.

4. The knee bracing system of claim 3 wherein the first distal-leg-retaining strap comprises tendon-retaining means, the tendon-retaining means for restricting movement of a patellar tendon and thus for further enhancing patellar function.

5. The knee bracing system of claim 1 wherein the torsional spring elements each comprise a proximal end and a distal end, the proximal ends being angled from the distal ends at a variable spring angle and interconnecting the proximal and distal support aims via end-receiving posts, the end-receiving posts being fixedly attached to the proximal and distal support arms.

6. The knee bracing system of claim 1 wherein the core elements comprise an elastic material, the elastic material comprising a select spring stiffness, the select spring stiffness for restoring the core elements to a relaxed core equilibrium state, the torsional spring elements compressibly receiving the core elements thereby radially displacing the core elements and imparting spring core restorative forces, the spring core restorative forces for modifying the restorative resistance forces and reducing knee stress during knee extension.

7. The knee bracing system of claim 6 wherein the core elements are interchangeable with secondary core elements, the secondary core elements comprising varied spring stiffness coefficients, the varied spring stiffness coefficients for enabling the user to selectively modify the restorative resistance forces.

8. A knee brace, the knee brace for extensionally centering and enhancing patellar function, the knee brace comprising:

an upper bracket assembly, the upper bracket assembly comprising a proximal-anterior-leg-receiving bracket portion, a medial proximal support arm, and a lateral proximal support arm;

a lower bracket assembly, the lower bracket assembly comprising a distal-posterior-leg-receiving bracket portion, a medial distal support arm, and a lateral distal support arm; and first and second spring assemblies, the spring assemblies each comprising a torsional spring element, a core element, and assembly-fastening means, the torsional spring elements each comprising a proximal end and a distal end, the proximal end being variably angled from the distal end intermediate a relaxed spring angle and a fully actuated spring angle, the assembly-fastening means fastening the proximal and distal ends to the proximal and distal support arms such that the proximal support arms are variably angled relative to the distal support arms intermediate a relaxed arm angle and a fully actuated arm angle, the torsional spring elements receiving the core elements, the proximal-anterior-leg-receiving portion for receiving an upper leg, the distal-posterior-leg-receiving portion for receiving a lower leg, the torsional spring elements being actuable for imparting restorative resistance forces, the restorative resistance forces for enhancing quadriceps muscle contraction during knee extension, the enhanced quadriceps muscle contraction for centering the patella during knee extension, the knee brace thus for extensionally centering and enhancing patellar function.

9. The knee brace of claim 8 wherein the core elements comprise an elastic material, the elastic material comprising a select spring stiffness, the select spring stiffness for restoring the core elements to a relaxed core equilibrium state, the torsional spring elements compressibly receiving the core elements thereby radially displacing the core elements and imparting core restorative forces, the core restorative forces for modifying the restorative resistance forces and for reducing knee joint stress during knee extension.

10. The knee brace of claim 9 wherein the core elements are interchangeable with secondary core elements, the secondary core elements comprising varied spring stiffness coefficients, the varied spring stiffness coefficients for enabling the user to selectively modify the restorative resistance forces.

11. The knee brace of claim 10 wherein the upper and lower bracket assemblies comprise means for retaining the upper and lower bracket assemblies upon the upper and lower leg.

12. The knee brace of claim 11 wherein the means for retaining the upper and lower bracket assemblies upon the upper and lower leg are defined by adjustable retaining straps, the adjustable retaining straps comprising a proximal-posterior retaining strap and a distal-anterior retaining strap, the upper bracket assembly being cooperable with the proximal-posterior retaining strap and the lower bracket assembly being cooperable with the distal-anterior retaining strap.

13. The knee brace of claim 12 wherein the adjustable retaining straps comprise a proximal-anterior retaining strap, the lower bracket assembly comprising a distal end and a proximal end, the proximal-anterior retaining strap being cooperable with the proximal end and the distal-anterior retaining strap being cooperable with the distal end, the proximal-anterior and distal-anterior retaining straps for enhancing retention of the lower bracket assembly upon the lower leg.

14. The knee brace of claim 13 wherein the proximal-anterior retaining strap comprises tendon-retaining means, the tendon-retaining means for restricting movement of a patellar tendon and thus for further enhancing patellar function.

15. The knee brace of claim 9 comprising garment attachment means, the garment attachment means for removably attaching the knee brace to a separately anchored, leg-covering garment, the removably attached knee brace being restricted from axial displacement relative to the upper and lower leg, the garment attachment means thus for axially positioning the knee brace upon the upper and lower leg.

16. A knee brace, the knee brace for extensionally centering and enhancing patellar function, the knee brace comprising:
    an upper bracket assembly, the upper bracket assembly comprising a leg-receiving proximal bracket portion and proximal axial support structure, the proximal axial support structure extending distally from the proximal bracket portion;
    a lower bracket assembly, the lower bracket assembly comprising a leg-receiving distal bracket portion and distal axial support structure, the distal axial support structure extending proximally from the distal bracket portion; and
    a spring assembly, the spring assembly comprising a torsional spring element and an elastically compressible core element, the torsional spring element compressibly receiving the core element and comprising proximal and distal ends, the proximal and distal ends being attached to the proximal and distal axial support structures, the proximal and distal bracket portions for receiving an upper and lower leg, the torsional spring element being actuable for imparting restorative resistance forces, the core element for damping the restorative resistance forces, the damped restorative resistance forces for enhancing quadriceps muscle contraction during knee extension, the enhanced quadriceps muscle contraction for centering the patella during knee extension, the knee brace thus for extensionally centering and enhancing patellar function.

17. The knee brace of claim 16 wherein the core element is interchangeable with at least one secondary core element, the secondary core element comprising a varied spring stiffness coefficient, the varied spring stiffness coefficient for enabling the user to selectively damp the restorative resistance forces.

18. The knee brace of claim 16 comprising garment attachment means, the garment attachment means for removably attaching the knee brace to a separately anchored, leg-covering garment, the removably attached knee brace being restricted from axial displacement relative to the upper and lower leg, the garment attachment means thus for axially positioning knee brace upon the upper and lower leg.

19. A method for extensionally centering a patella and thus enhancing patellar function, the method comprising the steps of:
    damping a coil-shaped torsional spring element assembly via a centrally and coaxially received disc-shaped elastomeric member;
    bracing an upper and lower leg against proximal and distal ends of the coil-shaped torsional spring element assembly; and
    actuating the damped coil-shaped torsional spring element assembly via knee extension, the actuated and damped coil-shaped torsional spring element assembly providing damped resistance for enhancing quadriceps muscle contraction and reducing patellar joint stress during knee extension.

20. The method of claim 19 wherein the step of damping the coil-shaped torsional spring element is defined by selectively choosing a damping element, the damping element being cooperably associated with the coil-shaped torsional spring element for damping said coil-shaped torsional spring element.

21. The method of claim 20 wherein the damping element is selectively chosen from a damping element group, the damping element group comprising damping elements, the damping elements being fanned from varied elastic materials, the elastic materials comprising varied stiffness coefficients, the varied stiffness coefficients for selectively damping the coil-shaped torsional spring element.

22. The method of claim 21 wherein the damping element group comprises core elements, the core elements being compressibly and interchangeably receivable by the coil-shaped torsional spring element for damping the coil-shaped torsional spring element.

23. The method of claim 19 wherein the step of bracing the upper and lower leg against proximal and distal ends of the torsional spring element assembly comprises the steps of anchoring a leg-covering garment in superficial adjacency to the coil-shaped torsional spring element assembly and anchoring the coil-shaped torsional spring element assembly to the leg-covering garment.

* * * * *